United States Patent
Nelson

(10) Patent No.: US 7,267,651 B2
(45) Date of Patent: Sep. 11, 2007

(54) METHOD AND APPARATUS FOR BLOOD FLOW MEASUREMENT USING MILLIMETER WAVE BAND

(75) Inventor: David Nelson, Chassell, MI (US)

(73) Assignee: Board of Control of Michigan Technological Univ., Houghton, MI (US)

( * ) Notice: Subject to any disclaimer, the term of this patent is extended or adjusted under 35 U.S.C. 154(b) by 484 days.

(21) Appl. No.: 10/831,742

(22) Filed: Apr. 23, 2004

(65) Prior Publication Data

US 2004/0215086 A1    Oct. 28, 2004

Related U.S. Application Data

(60) Provisional application No. 60/466,020, filed on Apr. 25, 2003.

(51) Int. Cl.
*A61B 5/02* (2006.01)
(52) U.S. Cl. ........................ 600/504; 600/549
(58) Field of Classification Search ................ 600/504, 600/505–507, 549, 600
See application file for complete search history.

(56) References Cited

U.S. PATENT DOCUMENTS

| | | | | |
|---|---|---|---|---|
| 4,228,805 A | * | 10/1980 | Rosen et al. ................ | 600/504 |
| 4,859,078 A | * | 8/1989 | Bowman et al. ............. | 374/44 |
| 5,954,659 A | * | 9/1999 | Curley et al. ............... | 600/505 |
| 5,967,986 A | | 10/1999 | Cimochowski et al. | |
| 6,045,512 A | * | 4/2000 | Roteliuk et al. ............. | 600/505 |
| 6,047,216 A | | 4/2000 | Carl et al. | |
| 6,100,703 A | * | 8/2000 | Davidov et al. ............. | 324/631 |
| 6,173,197 B1 | * | 1/2001 | Boggett et al. .............. | 600/310 |
| 6,682,480 B1 | | 1/2004 | Habib et al. | |

OTHER PUBLICATIONS

Alekseev et al., "Distortion of Millimeter-Wave Absorption in Biological Media Due to Presence of Thermocouples and Other Objects," IEEE Trans. Biomed. Eng., Sep. 2001, pp. 1013-1019, vol. 48, No. 9.

Alekseev et al., "Local Heating of Human Skin by Millimeter Waves: A Kinetics Study," Bioelectromagnetics, 2003, pp. 571-581, Wiley-Liss, Inc.

Chen, et al., "Pulse-Decay Method for Measuring the Thermal Conductivity of Living Tissues," Journal of Biomech. Eng., Nov. 1981, pp. 253-260, vol. 103.

Fouquet, et al., "Blood Perfusion Estimation From Noninvasive Heat Flux Measurements," ASME HTD, 1993, pp. 53-60, vol. 268.

(Continued)

*Primary Examiner*—Max F. Hindenburg
*Assistant Examiner*—Karen E Toth
(74) *Attorney, Agent, or Firm*—Michael Best & Friedrich LLP

(57) ABSTRACT

A system and method that determines a blood flow rate in an area of a subject. The system includes a transmitter operable to transmit an electrical signal in the range of about 20 GHz to about 300 GHz to the area, a temperature sensor positioned adjacent the area, and a processor operable to determine the blood flow rate in the area based on the rate of change of temperature in the area as a result of the application of the electrical signal on the area and a power density value.

10 Claims, 3 Drawing Sheets

OTHER PUBLICATIONS

Liu et al., "Sinusoidal Heating Method to Noninvasively Measure Tissue Perfusion," IEEE Trans. Biomed. Eng., Aug. 2002, pp. 867-877, vol. 49, No. 8.

Nelson et al., "Inter-Species Extrapolation of Skin Heating Resulting from Millimeter Wave Irradiation: Modeling and Experimental Results," Health Physics, May 2003, pp. 608-615, vol. 84, No. 5.

Nikawa et al., "Study on Dental Diagnosis and Treatment Using Millimeter Waves," IEEE Transactions on Microwave Theory and Techniques, Nov. 2000, pp. 1783-1788, vol. 48, No. 11.

Ryan et al., "Radio Frequency Radiation of Millimeter Wave Length: Potential Occupational Safety Issues Related to Surface Heating," Health Physics, 2000, pp. 170-181, vol. 78, No. 2.

Valvano et al., "The Simultaneous Measurement of Thermal Conductivity, Thermal Diffusivity, and Perfusion in Small Volumes of Tissue," Journal of Biomech. Eng., Aug. 1984, pp. 192-197, vol. 106.

Valvano et al., "An Isolated Rat Liver Model for the Evaluation of Thermal Techniques to Quantify Perfusion," Journal of Biomech. Eng., Aug. 1984, pp. 187-191, vol. 106.

Walters et al., "Heating and Pain Sensation Produced in Human Skin by Millimeter Waves: Comparison to a Simple Thermal Model," Health Physics, Mar. 2000, pp. 259-267, vol. 78, No. 3.

Walters et al., "Effects of Blood Flow on Skin Heating Induced by Millimeter Wave Irradiation in Humans," Health Physics, Jan. 2003, pp. 1-6, vol. 86, No. 1.

Welch et al., "Significance of Blood Flow in Calculations of Temperature in Laser Irradiated Tissue," IEEE Trans. Biomed. Eng., Mar. 1980, pp. 164-165, vol. BME 27, No. 3.

* cited by examiner

METHOD AND APPARATUS FOR BLOOD FLOW MEASUREMENT USING MILLIMETER WAVE BAND

RELATED APPLICATIONS

This application claims priority to U.S. Provisional Patent Application No. 60/466,020, filed Apr. 25, 2003. The contents of Application No. 60/466,020 are hereby incorporated by reference.

BACKGROUND OF THE INVENTION

Various techniques to measure blood flow are known, such as occlusion plethysmography, laser doppler imaging and laser speckle imaging, and thermal dilution measurement. The occlusion plethysmography technique requires restricting venous outflow from a limb, usually the arm. This method of measuring blood flow has disadvantages, such as, occluding blood flow in the entire arm, the blood flow measurements are non-local and slow, and the subject experiences discomfort as a result of the occlusion (e.g., tourniquet).

The laser doppler imaging and laser speckle imaging technique utilizes a laser beam that is incident on the skin. The reflection of the laser beam measures the flow of red blood cells rather than actual blood flow. These two imaging techniques do not provide accurate measurements of blood flow per unit tissue volume and the time for taking the measurements is relatively slow.

The thermal dilution measurement technique requires a heating element in contact with or underneath the skin and a thermocouple or thermistor to measure a temperature change of the skin surface. This technique measures how quickly the skin cools.

BRIEF DESCRIPTION OF THE INVENTION

In one embodiment, the invention includes a method of calculating a blood flow rate in an area. The method comprises the acts of generating an electrical signal having a power output, irradiating the area with the electrical signal, determining an incident power density of the electrical signal as a function of the power output and dimensions of the area being irradiated, heating the area in response to irradiating the area, sensing the temperature of the area within a time period, calculating the rate of temperature change of the area, and calculating the blood flow rate in the area based on the power density of the electrical signal and the rate of temperature change of the area.

In another embodiment, the invention includes a system for calculating blood flow rate in an area. The system comprises a transmitter operable to generate an electrical signal to irradiate the area, the electrical signal having a predetermined power, a temperature sensor operable to be positioned adjacent to the area and to sense the change in temperature of the area over time, and a processor coupled to the transmitter and the temperature sensor, the processor operable to compute the blood flow rate in the area based on the power of the electrical signal, a size of the area, and the rate of change in temperature of the area.

In yet another embodiment, the invention includes a method comprising the acts of applying an electrical signal to an area of a tissue, detecting a change of temperature in the area of the tissue over a period of time while the electrical signal is applied to the area of the tissue, the electrical signal having an incident power density, and determining a health status of a person based on the power density of the electrical signal and the change in temperature value.

DETAILED DESCRIPTION

Figure 1:
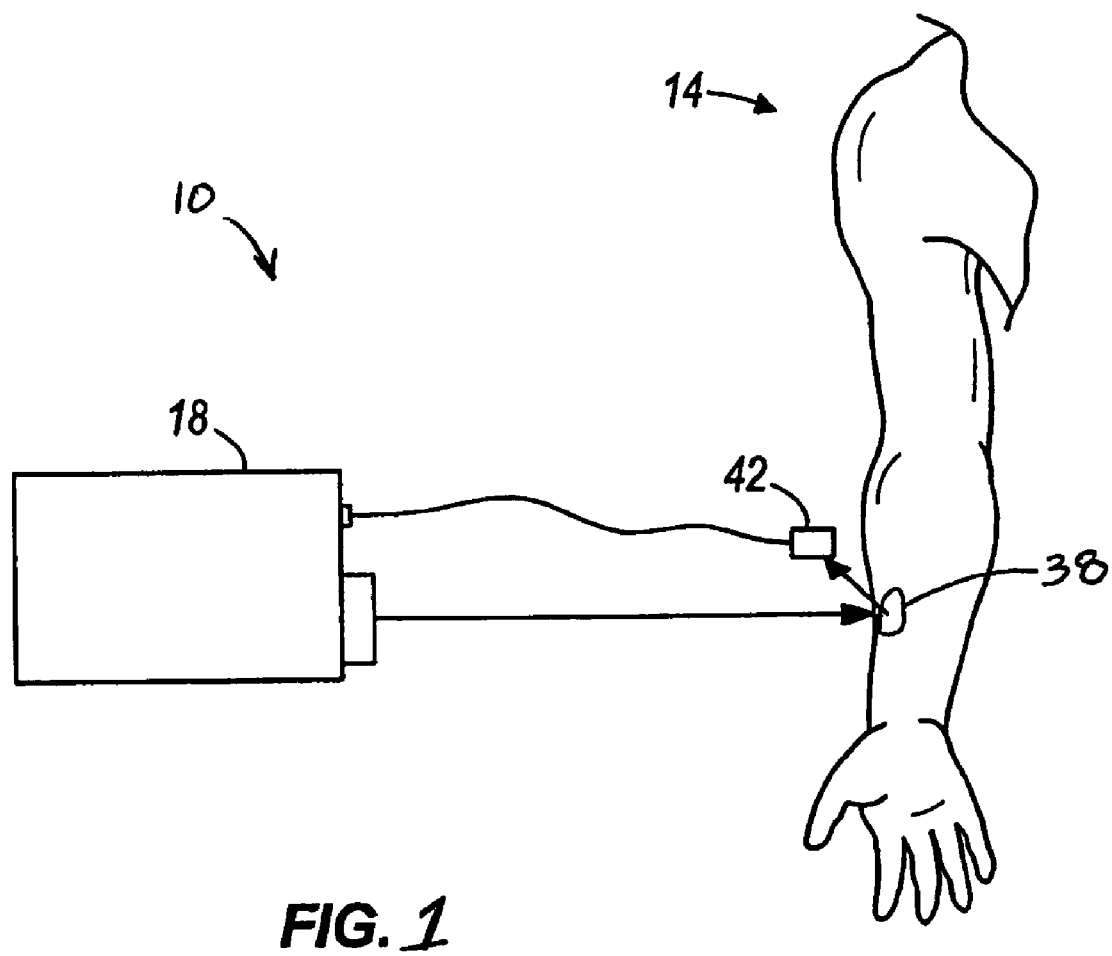
FIG. 1 illustrates a blood flow measurement device used on a subject according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a system 10 according to one embodiment of the invention that can determine a blood flow rate per unit volume in a human subject 14. For example, the system 10 can determine a blood flow rate per unit volume of skin and/or mucosa. Although FIG. 1 illustrates a human patient as the subject 14, the invention is applicable to animals other than humans. The invention is also applicable to non-living subjects, provided the non-living subject has a porous surface or another type of surface that permits the subject to heat and cool in response to irradiation and the flow of fluid within the subject. Also, the invention is not limited to measuring absolute blood flow rates, but may be used to monitor or measure absolute or relative flow rates of other fluids. For example, and without limiting the foregoing, the invention may have applications in measuring the absolute or relative flow rate of water, refrigerant, coolant, lymph, and other organic fluids that may flow within an animal, plant, or non-living subject.

Generally, with respect to a human subject, the rate of temperature increase for exposed tissue is a function of the frequency and the power density (which may, for example, be measured in Watts per square centimeter or $W/cm^2$) of radio frequency ("RF") radiation, the orientation of the subject tissue with respect to the electromagnetic field, and the properties of the target tissue (tissue permittivity at the exposure frequency, thermal diffusivity). More specifically, the rate of temperature increase of a skin surface, at a low power application of an RF electrical signal, is a function of the rate of blood flow to the underlying tissues. A non-contact device for the quantitative measurement of skin blood flow rate and the dermal microvascular response to thermal stimuli can be used to assess medical conditions and for the management of chronic diseases, such as, for example and without limitation, continuing assessment of peripheral circulation in diabetic patients, peripheral vascular disease, ovarian hyperstimulation syndrome, Raynaud's disease, and the loss of thermoregulatory function associated with aging and spaceflight. The measurement of skin blood flow rate can also be used to assess emergent medical conditions, such as (without limitation) circulatory shock and heat stroke. The measurement of skin blood flow rate can also be used to assist medical personnel in post-surgical evaluations of arterial patency of skin flaps.

Figure 2:
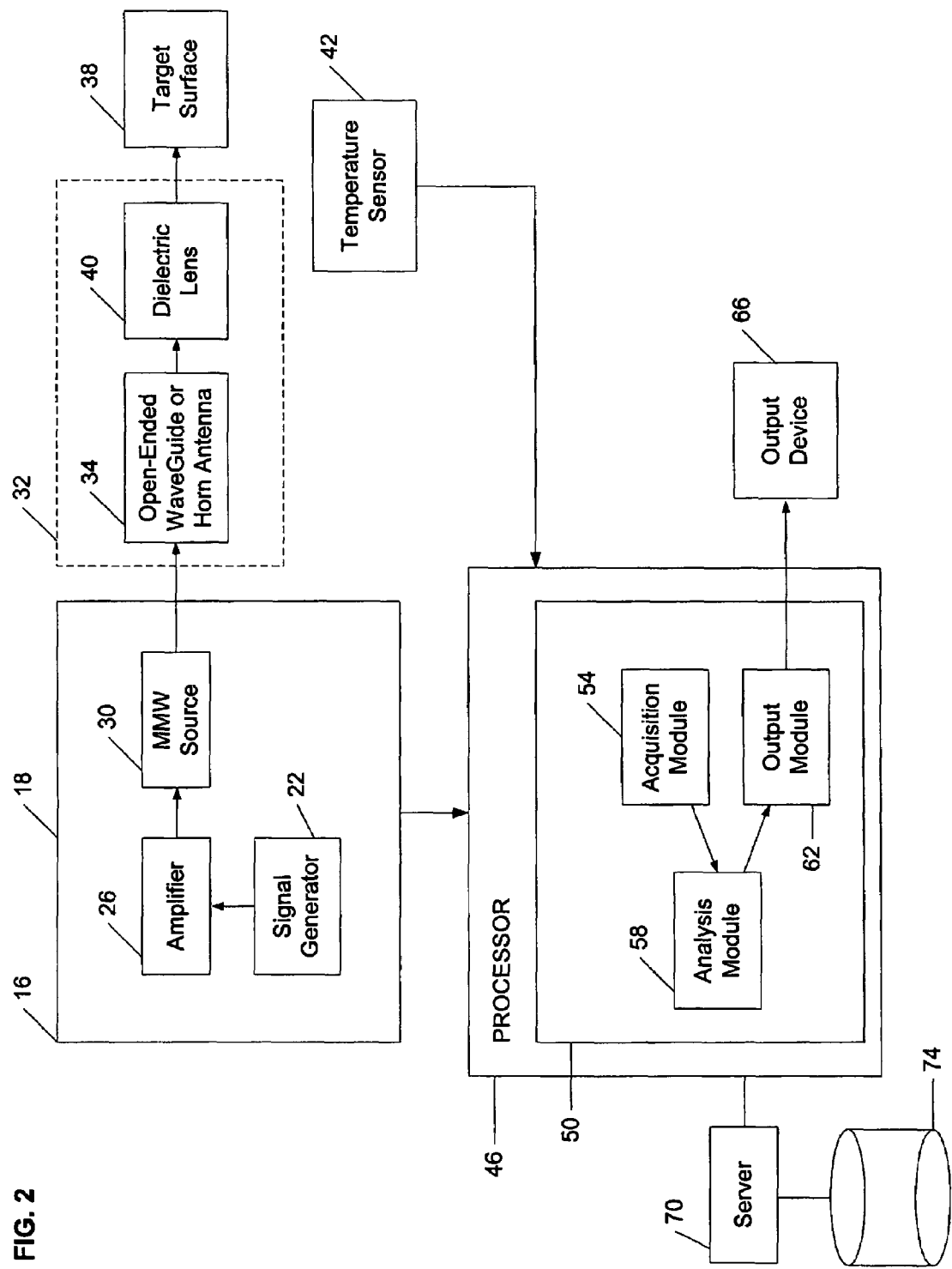
FIG. 2 is a block diagram of the blood flow measurement device of FIG. 1 according to one embodiment of the invention.

The modules and components of one embodiment of the invention are illustrated in FIG. 2, and will be described in detail below. Other embodiments of the invention can include fewer or more modules, and/or components. In addition, it should be noted that the functions of each module and/or component can be performed by hardware and/or software and/or a combination of hardware and software.

As shown in FIG. 2, an embodiment of the system 10 can include a transmitter 18, which can include a signal generator 22 (a suitable signal generator is an Agilent E8247C available from Agilent Technologies, Inc.), an amplifier 26 (e.g., RF amplifier), and a source module 30 (a suitable source module is an Agilent 83558A available from Agilent Technologies, Inc.). The transmitter 18 can be supported in a housing 16. The signal generator 22 can generate an electrical signal having a frequency in the radio frequency portion of the electromagnetic spectrum (e.g., about 10 kHz to about 300 GHz). More specifically, the signal generator 22 can generate an electrical signal having a frequency generally within the millimeter wave band. As used herein, the term "millimeter wave band" means 30 GHz to about 300 GHz, which in some instances may alternatively be referred to as the extremely high frequency (EHF) band or the near-infrared wave band, depending on how one defines those terms.

Generally, the electrical signal is low power. As used herein, the term "low power" means a power output that provides an incident power density of less than 1 $W/cm^2$ of the projected surface area normal to the direction of propagation.

The system 10 can also include an electrical signal modifier 32, which may include an open-ended waveguide and/or a horn antenna (individually and collectively referred to with reference number 34 in FIG. 2). The open-ended waveguide 34 may be, for example, a tube or duct constructed of copper or another conductive material. The dimensions of the open-ended waveguide 34 can vary depending on the frequency of the electrical signal to be transmitted. The open-ended waveguide 34 is electrically connected to the transmitter 18 to receive the electrical signal and to provide the electrical signal to a target surface 38 (i.e., the portion of the tissue that is exposed to the signal) on the subject 14. The target surface 38 can include multiple layers and thicknesses and is not limited to the top or surface that contacts the electrical signal. The horn antenna 34 may be, for example, a funnel-shaped component that is electrically connected to the transmitter 18 to receive the electrical signal. The horn antenna 34 would modify the spatial distribution of the electrical signal and therefore provide the electrical signal to a larger target surface 38 than the target surface 38 of the waveguide.

The electrical signal irradiates the target surface 38. The electrical signal has an associated power density value when applied to the target surface 38. The power density is a function of the electrical signal power and the dimensions of the target area, and is contemplated to be generally less than about 1 $W/cm^2$ when used to irradiate the skin tissue of a human subject 14. The incident power density of the electrical signal on the target surface 38 is a function of the electrical signal power, the dimensions of the target surface 38, and the angle of incidence of the electrical signal with respect to the target surface 38. The angle of incidence of the electrical signal can affect the amount of energy from the electrical signal that the target surface 38 can absorb. The target surface 38 has an associated absorption coefficient, which is a fraction of the incident energy that is absorbed by the medium of the target surface 38. The absorption coefficient can vary with the frequency of the electrical signal. Generally, the target surface 38 is planar and the angle of incidence of the electrical signal is equal to or less than 90 degrees. The absorption coefficient of a non-planar surface can also be determined.

Some transmitters 18 are intended to operate at a fixed power density, which means that the power output of the electrical signal is fixed, and the targeted surface 38 is expected to be maintained at a preselected and fixed distance from the transmitter 18. If the transmitter 18 is not intended to operate at a fixed power density, the system 10 may include a means for calibrating the transmitter 18 to accommodate changes in the environment surrounding the transmitter 18 or changes in the parameters of the blood flow rate measurement procedure. For example, the transmitter 18 may include a means for calibrating that permits the power and/or frequency of the electrical signal to be adjusted.

The system 10 can also include a dielectric lens 40 positioned between the transmitter 16 and the target surface 38 to focus the electrical signal to a smaller target surface size. The dielectric lens 40 could allow for the use of a lower power transmitter 18 since a smaller irradiated surface area requires proportionally less power. Because the dielectric lens 40 modifies the electrical signal, it is deemed part of the electrical signal modifier 32 as seen in FIG. 2. The dielectric lens 40 may be used with or without one or both of the wave guide 34 and horn antenna 34 to modify the dimensions, size, shape, intensity, and cross-sectional area of the dispersion pattern of the electrical signal.

The system 10 can further include a temperature sensor 42, such as a thermocouple, transducer, thermistor, infrared thermography camera (a suitable camera is a ThermaCam S40 available from FLIR Systems in Danderyd, Sweden or a Radiance I infrared camera system available from Amber Engineering, Inc., in Goleta Calif.), infrared sensor or other component operable to sense a temperature of the target surface 38. The temperature sensor 42 can be positioned adjacent to the target surface 38 to sense/detect a temperature change as a result of the application of the electrical signal on the target surface 38. As used herein with respect to the temperature sensor 42, the term "adjacent" means positioned close enough to the target surface 38 to accurately sense a temperature of the target surface 38, whether or not the temperature sensor 42 actually touches the target surface 38.

The frequency and the properties of the target surface 38 affect the penetration depth of the electrical signal in the target surface 38. Penetration depth is the depth at which power density has decreased to 37% of the power density at the surface. Generally, the penetration depth of human skin is in the range of about 0.1 mm to about 1.0 mm for frequencies in the range of about 300 GHz to about 30 GHz, respectively. The system 10 measures the rate of blood flow in the target surface 38.

The system 10 can include a processor 46, which is electrically connected to the temperature sensor 42. The processor 46 can include circuitry (not shown), such as a signal conditioning circuit, to receive and/or process the signal(s) from the temperature sensor 42. The processor 46 can be electrically connected to the transmitter 16 and/or the data, such as the characteristics of the electrical signal, from the transmitter 16 can be manually entered into the processor 46. The processor 46 can be a computer or any other device operable to receive data, manipulate data, perform calculations, display information, and/or perform similar functions. The processor 46 can include I/O interfaces and storage devices or memory. The processor communicates and receives commands from input devices such as a keyboard and a mouse.

The processor 46 can include a software program 50. The software program 50 can include an acquisition module 54, an analysis module 58, and an output module 62. As noted above, the function and operation of the software program 50 can be encompassed in suitable hardware components and/or modules. The acquisition module 54 is operable to acquire and receive data manually entered into the processor 46 and data from the temperature sensor 42 and the transmitter 18. The analysis module 58 is electrically connected to the acquisition module 54. The analysis module 58 is operable to receive the data from the acquisition module 54 and analyze the data. The analysis module 58 can perform any mathematical function, manipulate the data, correlate the data, format the data, and/or perform any other analysis technique. The output module 62 can be electrically connected to the acquisition module 54 and/or the analysis module 58. The output module 62 is operable to receive data from the acquisition module 54, receive data from the analysis module 58, format the data, and output the data to a monitor, a display, and/or a printer (collectively referred to as an output device 66).

As illustrated in FIG. 2, an embodiment of the system 10 has been described and illustrated as including various devices, modules, and/or components. It should be noted that the system 10 can be incorporated as a single device including the various modules and/or components described herein. It should also be noted that the system 10 can be handheld, mounted to a support structure, such as a wall, supported on a moveable item, such as a rack, a cart, or other like item, or be free-standing.

The system 10 can include a server 70 and/or a database 74 for storing information related to blood flow data. The server 70 can include an operating system for running various software programs and/or a communications application. The software programs can be manipulated by computer terminals (not shown) and/or medical equipment to acquire, enter, review, and/or save information. The processor 46 can interface with and/or connect to the server to upload information and/or download information. In addition, the software program 50 can reside on the server 70.

Figure 3:
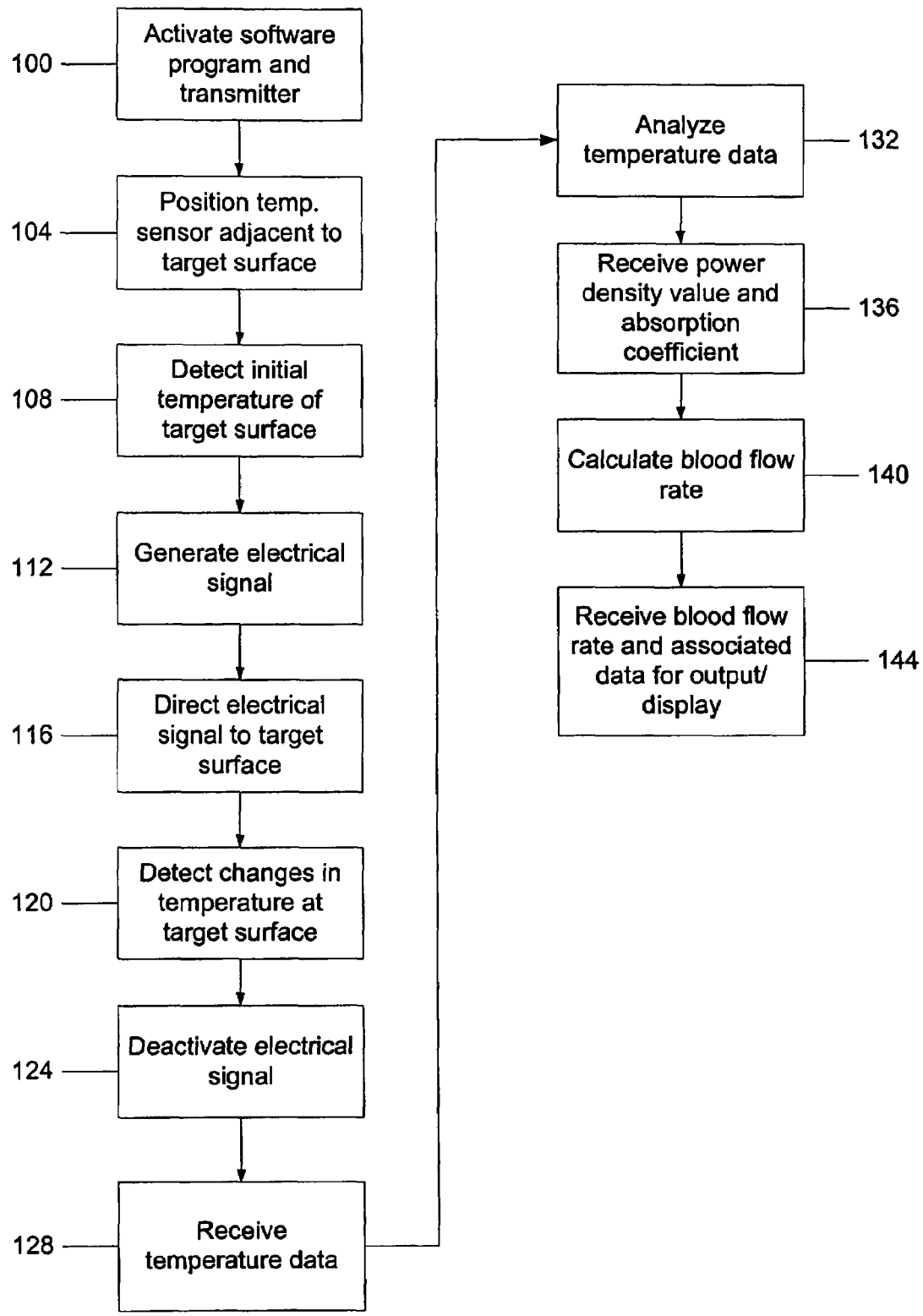
FIG. 3 is a flow chart illustrating the operation of the blood flow measurement device of FIG. 2 according to one embodiment of the method of the invention.

FIG. 3 is a flow chart illustrating one embodiment of the method of the invention. In preparation for determining a blood flow rate of a target surface 38, the system 10 can activate (at 100) the software program 50 and the transmitter 18. In addition, the temperature sensor 42 can be positioned (at 104) adjacent to the target surface 38. The processor 46 can communicate with the temperature sensor 42 to measure (at 108) an initial temperature of the target surface 38. The initial temperature can be determined by taking a plurality of measurements over a period of time. The transmitter can generate (at 112) an electrical signal having a frequency in the radio frequency portion of the electromagnetic spectrum. More specifically, the electrical signal may be provided in some instances in the millimeter wave band or may go outside of the millimeter wave band (e.g., as low as 20 GHz for some applications).

The electrical signal is directed (at 116) by the transmitter 18 toward the target surface 38. The electrical signal can be modified by entering the electrical signal modifier 32 to accommodate the desired size of the target surface 38. The target surface 38 changes temperature (e.g., heats or cools) as a result of the application of the electrical signal to the target surface 38. The temperature sensor 42 can detect (at 120) the changes in temperature of the target surface 38 over a period of time. For example, the temperature sensor 42 can detect a change in temperature of the target surface 38 every second or any other suitable time measurement. For the application to human subjects, the time period over which the electrical signal is applied and during which the temperature sensor 42 detects temperature changes of the target area is typically less than one minute. It should be noted, however, that the electrical signal can be applied to the target surface 38 longer than one minute and the temperature sensor 42 can detect temperature changes of the target surface 38 beyond the one minute time period. For example, the thermoregulatory response of the subject 14 can be measured during a one minute or longer application of the electrical signal on the target surface 38. The electrical signal can be deactivated (at 124).

The acquisition module 54 of the processor 46 can receive (at 128) the temperature data from the temperature sensor 42. The analysis module 58 can analyze (at 132) the temperature data to determine the rate of change in temperature of the target surface 38 over the period of time that the electrical signal was applied to the target surface 38. The analysis module 58 can receive (at 136) a power density value and an absorption coefficient that is either manually entered into the processor 46 and/or received from the transmitter 16. For example, the user may enter into the processor 46 a value for the size of the target surface 38 in square centimeters, or the processor 46 may receive a fixed power density value from the transmitter 16.

The analysis module can calculate (at 140) a blood flow rate in the target surface 38 based on the temperature data (e.g., the rate of change of the temperature) and the power density value. The output module can receive (at 144) the blood flow rate and associated data for formatting (formatting the data is optional) and transfer to the output device 66. The output device 66 can display and/or print the data. The data can be formatted to include raw data, measurements, unanalyzed data, analyzed data, images, charts, graphs, identified abnormalities, normal and abnormal ranges, patient identifiers (e.g., name, age, sex, weight, race), patient history (e.g., cholesterol level, diabetes, family history, smoking, blood pressure, obesity), symptoms, dates of reports and tests, and identification of prescribing, attending and reading physicians, etc. The blood flow rate data can be used to provide a health assessment of the subject 14

Various features and advantages of the invention are set forth in the following claims.

What is claimed is:

1. A method of calculating a blood flow rate in an area, the method comprising:
    generating an electrical signal having a power output;
    irradiating the area with the electrical signal;
    determining an incident power density of the electrical signal as a function of the power output and dimensions of the area being irradiated;
    heating the area in response to irradiating the area;
    sensing the temperature of the area within a time period;
    calculating the rate of temperature change of the area;
    determining an absorption coefficient; and
    calculating the blood flow rate in the area based on the power density of the electrical signal, the absorption coefficient, and the rate of temperature change of the area;
    wherein the electrical signal includes a frequency in the millimeter wave band.

2. The method as claimed in claim 1 wherein the electrical signal includes a frequency in the range of about 80 GHz to about 120 GHz.

3. The method as claimed in claim 1 wherein the area is a tissue of a human.

4. The method as claimed in claim 1 wherein the act of irradiating the area with the electrical signal includes the act of continuously irradiating the area with the electrical signal.

5. The method as claimed in claim 1 wherein the act of irradiating the area includes the act of irradiating the area with the electrical signal to a penetration depth in the range of about 0.1 mm to about 1.0 mm.

6. The method as claimed in claim 1 wherein the incident power density of the electrical signal is less than approximately 1 W/cm$^2$.

7. The method as claimed in claim 1 further comprising the act of modifying at least one dimension of the electrical signal prior to the act of irradiating the area.

8. The method as claimed in claim 1 wherein the act of calculating the rate of temperature change of the area occurs simultaneously with the act of irradiating the area.

9. The method as claimed in claim 1 wherein the act of irradiating the area includes the act of directing the electrical signal in a direction that is perpendicular with respect to the area.

10. The method as claimed in claim 1 further comprising the acts of sensing the temperature of the area, calculating the rate of temperature change of the area, and calculating the blood flow rate in the area based on the power density of the electrical signal, the absorption coefficient, and the rate of temperature change in the area after deactivating the electrical signal.

* * * * *